US00PP20653P2

(12) United States Plant Patent
ter Laak

(10) Patent No.: US PP20,653 P2
(45) Date of Patent: Jan. 19, 2010

(54) ***BEGONIA* PLANT NAMED 'VICTORIA FALLS'**

(50) Latin Name: *Begonia pendula*
Varietal Denomination: Victoria Falls

(75) Inventor: Wendela Antoinette ter Laak, Amstelveen (NL)

(73) Assignee: Florema Young Plants B.V., Amstelveen (NL)

( * ) Notice: Subject to any disclaimer, the term of this patent is extended or adjusted under 35 U.S.C. 154(b) by 0 days.

(21) Appl. No.: 12/228,283

(22) Filed: Aug. 11, 2008

(51) Int. Cl.
*A01H 5/00* (2006.01)

(52) U.S. Cl. ..... Plt./347

(58) Field of Classification Search ..... Plt./347
See application file for complete search history.

*Primary Examiner*—June Hwu
(74) *Attorney, Agent, or Firm*—C. A. Whealy

(57) ABSTRACT

A new and distinct cultivar of *Begonia* plant named 'Victoria Falls', characterized by its compact, pendulous and mounded plant habit; freely basal branching habit; pubescent leaves; and numerous double flowers that are bright orange in color.

1 Drawing Sheet

Botanical designation: *Begonia pendula.*
Cultivar denomination: 'Victoria Falls'.

BACKGROUND OF THE INVENTION

The present invention relates to a new and distinct cultivar of *Begonia* plant, botanically known as *Begonia pendula*, commercially known as hybrid tuberose *Begonia*, and hereinafter referred to by the name 'Victoria Falls'.

The new *Begonia* plant is a product of a planned breeding program conducted by the Inventor in Amstelveen, The Netherlands. The objective of the breeding program was to develop new freely branching hybrid tuberose *Begonia* cultivars with numerous brightly-colored flowers.

The new *Begonia* plant originated from a cross-pollination made by the Inventor in December, 2006 of a proprietary selection of *Begonia pendula* identified as code number 03-H-27, not patented, as the female, or seed, parent with a proprietary selection of *Begonia pendula* identified as code number 03-66-3, not patented, as the male, or pollen, parent. The new *Begonia* was discovered and selected by the Inventor from within the progeny of the stated cross-pollination in a controlled greenhouse environment in Amstelveen, The Netherlands in May, 2007.

Asexual reproduction of the new *Begonia* by cuttings in a controlled greenhouse environment in Amstelveen, The Netherlands since July, 2007, has shown that the unique features of this new *Begonia* plant are stable and reproduced true to type in successive generations.

SUMMARY OF THE INVENTION

Plants of the new *Begonia* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Victoria Falls'. These characteristics in combination distinguish 'Victoria Falls' as a new and distinct cultivar of *Begonia:*

1. Compact, pendulous and mounded plant habit.
2. Freely basal branching habit.

3. Pubescent leaves.
4. Numerous double flowers that are bright orange in color.

Plants of the new *Begonia* can be compared to plants of the female parent selection. Plants of the new *Begonia* differ from plants of the female parent selection in the following characteristics:

1. Plants of the new *Begonia* are more vigorous than plants of the female parent selection.
2. Plants of the new *Begonia* have pubescent leaves whereas plants of the female parent selection have glabrous leaves.
3. Plants of the new *Begonia* have larger flowers than plants of the female parent selection.
4. Flower color of plants of the new *Begonia* is more intense than flower color of plants of the female parent selection.

Plants of the new *Begonia* can be compared to plants of the male parent selection. Plants of the new *Begonia* differ from plants of the male parent selection in the following characteristics:

1. Plants of the new *Begonia* are larger than plants of the male parent selection.
2. Leaves of plants of the new *Begonia* are lighter green in color than leaves of plants of the male parent selection.
3. Flowers of plants of the new *Begonia* have more tepals than flowers of plants of the male parent selection.
4. Plants of the new *Begonia* and the male parent selection differ in flower color as plants of the male parent selection have red-colored flowers.

Plants of the new *Begonia* can also be compared to plants of the *Begonia* 'Encanto Orange', not patented. In side-by-side comparisons conducted in Amstelveen, The Netherlands, plants of the new *Begonia* differed from plants of 'Encanto Orange' in the following characteristics:

1. Plants of the new *Begonia* had shorter and broader leaves than plants of 'Encanto Orange'.
2. Plants of the new *Begonia* had pubescent leaves whereas plants of 'Encanto Orange' had glabrous leaves.
3. Plants of the new *Begonia* had double flowers whereas plants of 'Encanto Orange' had single flowers.

4. Plants of the new *Begonia* had larger flowers than plants of 'Encanto Orange'.
5. Flowers of plants of the new *Begonia* were darker orange in color than flowers of plants of 'Encanto Orange'.

BRIEF DESCRIPTION OF THE PHOTOGRAPH

The accompanying colored photograph illustrates the overall appearance of the new *Begonia*, showing the colors as true as it is reasonably possible to obtain in colored reproductions of this type. Colors in the photograph may differ slightly from the color values cited in the detailed botanical description which accurately describe the colors of the new *Begonia*.

The photograph comprises a side perspective view of a typical flowering plant of 'Victoria Falls' grown in a container.

DETAILED BOTANICAL DESCRIPTIONS

Plants used for the aforementioned photograph and following observations and measurements were grown in Rijsenhout, The Netherlands in 12-cm containers and under commercial practice in a glass-covered greenhouse during the spring and summer. During the production of the plants, day and night temperatures ranged from 15° C. to 20° C and maximum light levels were 18,000 lux. Plants had been growing for four months when the photograph and the description were taken. In the following description, color references are made to The Royal Horticultural Society Colour Chart, 2001 Edition, except where general terms of ordinary dictionary significance are used.

Botanical classification: *Begonia pendula* 'Victoria Falls'.

Parentage:

*Female, or seed, parent.*—Proprietary selection of *Begonia pendula* identified as code number 03-H-27, not patented.

*Male, or pollen, parent.*—Proprietary selection of *Begonia pendula* identified as code number 03-66-3, not patented.

Propagation:

*Type.*—By terminal vegetative cuttings.

*Time to initiate roots.*—About 15 days at temperatures of about 20° C.

*Time to produce a rooted young plant.*—About 14 to 18 days at temperatures of about 20° C.

*Root description.*—Medium in thickness, fibrous; white in color. Plants of the new *Begonia* have not been observed to form tubers.

*Rooting habit.*—Freely branching; moderately dense.

Plant description:

*Plant form and growth habit.*—Compact, pendulous and mounded plant habit; freely basal branching with about five to six primary branches per plant; primary branches with secondary branches at potentially every node. Moderately vigorous and moderate growth rate.

*Plant height.*—About 15 cm to 20 cm.

*Plant width.*—About 35 cm to 40 cm.

*Branch description.*—Length: About 10 cm to 15 cm. Diameter: About 6 mm. Internode length: About 3 cm. Texture: Pubescent. Color: Close to 173B.

*Leaf description.*—Arrangement: Alternate, simple. Length: About 8 cm to 12 cm. Width: About 5 cm to 6 cm. Shape: Deltoid to ovate. Apex: Acuminate. Base: Obliquely cordate. Margin: Serrate. Texture, upper and lower surfaces: Pubescent; rough. Venation pattern: Palmate; reticulate. Color: Developing and fully expanded leaves, upper surface: Close to 132C; venation, close to 136C. Developing and fully expanded leaves, lower surface: Close to 131D; venation, close to 136C. Petioles: Length: About 5 cm to 7 cm. Diameter: About 4 mm. Texture, upper and lower surfaces: Smooth, glabrous. Color, upper surface: Close to 132C. Color, lower surface: Close to 131D.

Flower description:

*Flowering habit.*—Rounded double flowers with numerous tepals arranged in cymes. Freely flowering habit with about four to five flowers and flower buds per cyme. Flowers pendulous and face mostly outwardly or downward.

*Fragrance.*—Not detected.

*Natural flowering season.*—Plants flower continuously during the summer in The Netherlands.

*Flower longevity.*—Flowers last about four weeks on the plant; flowers persistent.

*Inflorescences.*—Height: About 4 cm to 5 cm. Diameter: About 7 cm to 9 cm.

*Flowers.*—Diameter: About 4 cm to 6 cm. Depth (height): About 1 cm to 2 cm.

*Flower buds.*—Shape: Ovoid. Length: About 1 cm to 2 cm. Diameter: About 2. cm to 3 cm. Color: Close to 33B.

*Tepals.*—Arrangement: Rosette. Quantity per flower: Usually about 10 to 15 per flower arranged in several whorls. Length: About 2 cm to 3 cm. Width: About 3 cm to 4 cm. Shape: Obovate to rounded. Apex: Rounded, obtuse. Base: Cordate. Margin: Entire; undulate. Texture, upper and lower surfaces: Smooth, glabrous; velvety. Color: When opening, upper and lower surfaces: Close to 33B. Fully opened, upper and lower surfaces: Close to 33A; color does not fade with development.

*Flower bracts.*—Quantity/arrangement: Two, opposite. Length: About 1 cm. Diameter: About 1 cm. Shape: Broadly ovate. Apex: Acute. Base: Obtuse. Margin: Entire; undulate. Texture, upper and lower surfaces: Glabrous, smooth. Color, upper surface: Close to 144D; towards the margin, close to 35A. Color, lower surface: Close to 145B; towards the margin, close to 35A.

*Peduncles.*—Angle: About 30° to 45° from vertical. Strength: Moderately strong. Length: About 4 cm to 5 cm. Diameter: About 3 mm to 4 mm. Texture: Smooth, glabrous. Color: Close to 179B.

*Pedicels.*—Angle: About 90° from the peduncle. Strength: Moderately strong. Length: About 4 cm to 6 cm. Diameter: About 2 mm to 3 mm. Texture: Smooth, glabrous. Color: Close to 168D.

*Reproductive organs.*—Stamens and pistils not observed.

*Seed/fruit.*—Seed and fruit production have not been observed.

Disease/pest resistance: Resistance to pathogens and pests common to *Begonia* has not been observed.

Temperature tolerance: Plants of the new *Begonia* have been observed to tolerate temperatures from about 10° C. to about 40° C.

It is claimed:

1. A new and distinct *Begonia* plant named 'Victoria Falls' as illustrated and described.

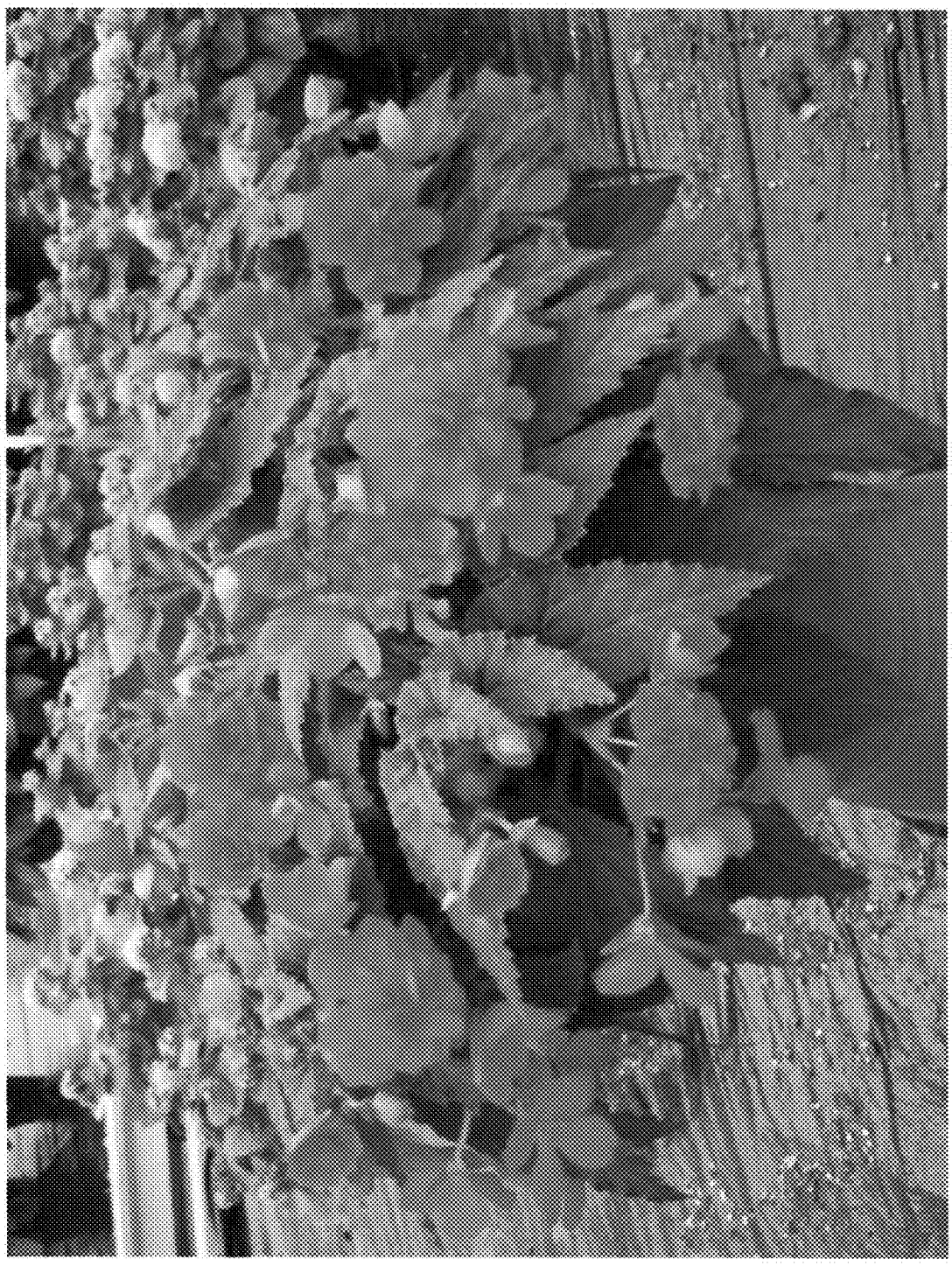

* * * * *